US012751925B2

(12) United States Patent
Chaudhuri et al.

(10) Patent No.: US 12,751,925 B2
(45) Date of Patent: Oct. 6, 2026

(54) POWDER MIXING DEVICE, AND USES THEREOF

(71) Applicant: University of Connecticut, Farmington, CT (US)

(72) Inventors: Bodhisattwa Chaudhuri, South Windsor, CT (US); Tanu Mehta, Willington, CT (US); Raj Mukherjee, Chattanooga, TN (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 532 days.

(21) Appl. No.: 18/366,363

(22) Filed: Aug. 7, 2023

(65) Prior Publication Data

US 2024/0041773 A1 Feb. 8, 2024

Related U.S. Application Data

(60) Provisional application No. 63/395,363, filed on Aug. 5, 2022.

(51) Int. Cl.
*A61K 9/16* (2006.01)
*A61K 31/192* (2006.01)
(Continued)

(52) U.S. Cl.
CPC .......... *A61K 9/1682* (2013.01); *A61K 9/1623* (2013.01); *A61K 31/192* (2013.01); *B01F 23/60* (2022.01); *B01F 29/40118* (2022.01); *B01F 35/3204* (2022.01); *B01F 35/43* (2022.01); *B01F 35/51* (2022.01); *B01F 2101/22* (2022.01); *B01F 2215/0472* (2013.01)

(58) Field of Classification Search
CPC ..... B01F 23/60; B01F 29/40118; B01F 35/51
See application file for complete search history.

(56) References Cited

U.S. PATENT DOCUMENTS

| | | | | |
|---|---|---|---|---|
| 3,362,688 A * | 1/1968 | Fischer | B01F 29/64 366/170.2 |
| 4,141,657 A * | 2/1979 | Fischer | B01F 29/62 366/232 |

(Continued)

FOREIGN PATENT DOCUMENTS

| | | | |
|---|---|---|---|
| GB | 986934 A * | 3/1965 | B01F 9/005 |

OTHER PUBLICATIONS

Matsusaka, S. et al., "Triboelectric charging of powers: A review", Chemical Engineering Science, vol. 65, Issue 22, Nov. 15, 2010, pp. 5781-5807, 6 pages.

(Continued)

*Primary Examiner* — Marc C Howell
(74) *Attorney, Agent, or Firm* — CANTOR COLBURN LLP

(57) ABSTRACT

A powder mixing device, having: a stand; a frame mounted to the stand, the frame being rotatable around a first axis of rotation; and a mixing vessel mounted to the frame, the mixing vessel being rotatable around the first axis of rotation; wherein the mixing vessel comprises at least two components, a first segment and a second segment, wherein the first segment has a work function higher or lower than a work function of the second segment, and a work function of a powder to be mixed is within the work function of the first segment and the second segment.

20 Claims, 10 Drawing Sheets

(51) Int. Cl.

| | |
|---|---|
| ***B01F 23/60*** | (2022.01) |
| ***B01F 29/00*** | (2022.01) |
| ***B01F 35/32*** | (2022.01) |
| ***B01F 35/43*** | (2022.01) |
| ***B01F 35/51*** | (2022.01) |
| *B01F 101/22* | (2022.01) |

(56) References Cited

U.S. PATENT DOCUMENTS 8,827,545 B2 * 9/2014 Kalidindi .......... B01F 29/40118 209/296
2015/0224424 A1 * 8/2015 Yano .................. H01M 50/414 206/524.1

OTHER PUBLICATIONS

Mehrotra, Amit et al., "Spontaneous Separation of Charged Grains", Physical Review Letters, PRL 99, 058001 (2007), The American Physical Society, 4 pages.

Mullarney et al., "Improving the prediction of exceptionally poor tableting performance: An investigation into Hiestand's special case", Journal of Pharmaceutical Sciences, vol. 93, Issue Aug. 8, 2004, pp. 2017-2021, ScienceDirect, 5 pages.

Naik, Shivangi et al., "An experimental and numerical modeling study of tribocharging in pharmaceutical granular mixtures", Powder Technology 297 (2016) 211-219, Elsevier, 9 pages.

Naik, Shivangi et al., Quantification of Tribocharging of Pharmaceutical Powders in V-Blenders: Experiments, Multiscale Modeling, and Simulations, Journal of Pharmaceutical Sciences 105 (2016) 1467-1477, Elsevier, 21 pages.

Palmer, K N, "Dust explosion Hazards in Pneumatic Transport", Fire Research Note No. 992, Oct. 1973, 21 pages.

Supuk, Enes et al., "Tribo-electrification of active pharmaceutical ingredients and excipients", Powder Technology, ScienceDirect, vol. 217, Feb. 2012, pp. 427-434; https://www.sciencedirect.com/science/article/abs/pii/S0032591011006024, 7 pages.

Walsh et al., "Playing hide and seek with poorly tasting paediatric medicines: Do not forget the excipients", Advanced Drug Delivery Reviews, vol. 73, Jun. 30, 2014, pp. 14-33, ScienceDirect, 52 pages.

* cited by examiner

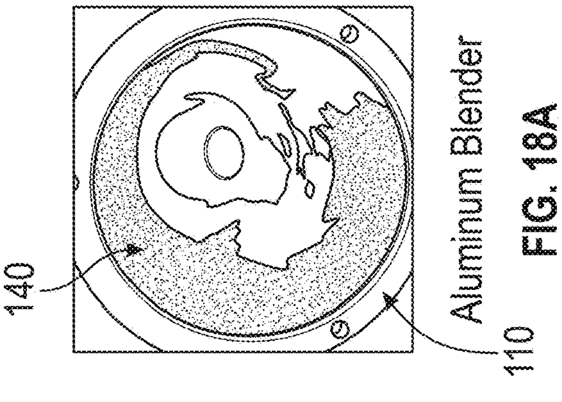
Aluminum Blender
FIG. 18A
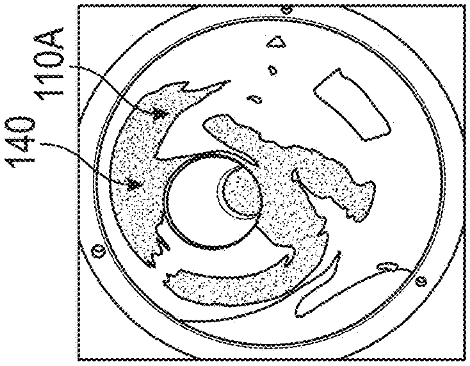
FIG. 18B1
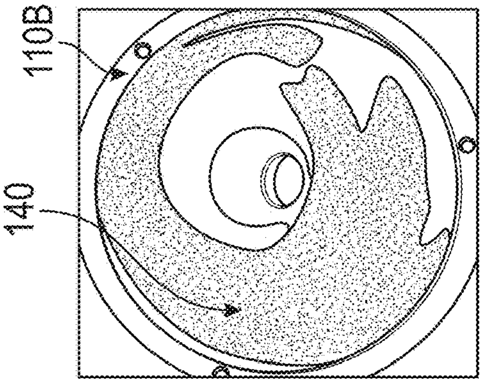
Blender (Al PVC)
FIG. 18B2
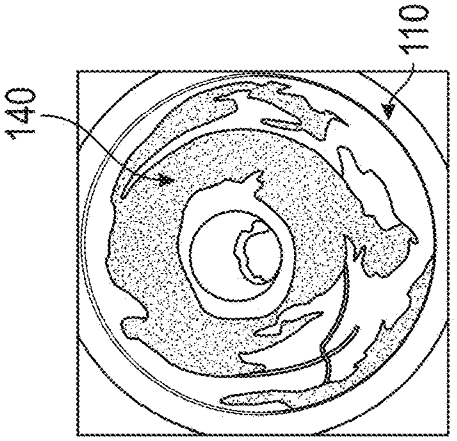
PVC Blender
FIG. 18C
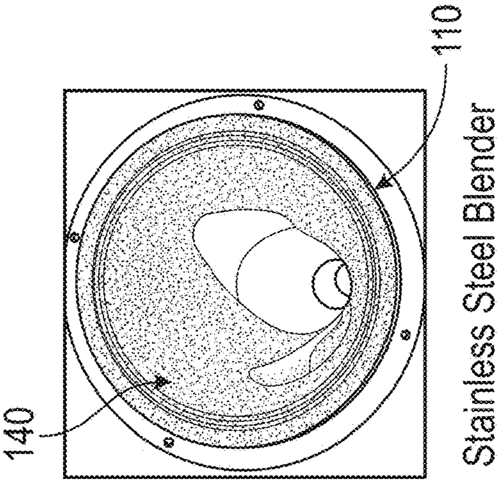
Stainless Steel Blender
FIG. 18D
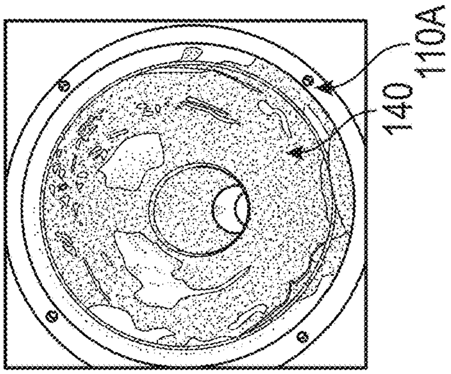
FIG. 18E1
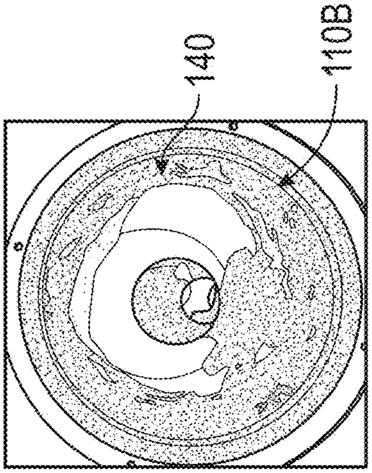
Blender (SS-PVC)
FIG. 18E2

POWDER MIXING DEVICE, AND USES THEREOF

CROSS REFERENCE

This application claims priority to U.S. 63/395,363, filed on May 5, 2022, the contents of which is incorporated herein by reference in its entirety.

FIELD OF THE DISCLOSURE

The disclosure relates to powder mixing devices of the type referred to as blenders, for use in various industries wherein it is required to intimately blend powdered or granular solid materials with other solid or liquid materials. More particularly, the subject disclosure relates to a device and its uses to mitigate tribocharging in powders encountered during blending or mixing process.

BACKGROUND

Pharmaceutical industry involves handling of powders on a large scale for manufacturing of solid dosage forms as they constitute 85% of the dosage forms due to their ease of manufacturing, packaging, longer shelf life, alterable drug release profiles, and high patient compliance. In order to manufacture a tablet, powders are processed through multiple unit operations such mixing, milling, granulation, drying and pneumatic transport. Mixing of powders is a common procedure employed in multiple industries including food, automotive, defense, cosmetics, polymer, agriculture, printing, and pharmaceuticals. The efficiency of these unit operations governs quality of the final product. During these unit operations powders get charged due to particle-particle collisions and particle-equipment wall collisions, impacting the performance of blending process. Electrostatic charging via contact electrification or tribocharging refers to the process of charging of two solid surfaces when they are brought into contact and separated. Considerable charge generation significantly affects granular flows creating industrial storage problems, jamming, segregation, and unfortunately, industrial fire explosions due to electrostatic discharge in the presence of volatile organic solvents.

BRIEF DESCRIPTION

Disclosed is a mixing vessel, including: a first segment having a first work function; and a second segment having a second work function that differs from the first work function, wherein the mixing vessel is configured for mixing a powder having a third work function that is between the first and second work functions.

In addition to one or more aspects of the vessel, or as an alternate, the first segment is an insulator.

In addition to one or more aspects of the vessel, or as an alternate, the first segment includes polymethyl methacrylate (PMMA), polyvinyl chloride (PVC), nylon, polytetrafluoroethylene (Teflon), or a combination thereof In addition to one or more aspects of the vessel, or as an alternate, the second segment is a metal or an alloy.

In addition to one or more aspects of the vessel, or as an alternate, the second segment includes Aluminum, stainless steel, or a combination thereof In addition to one or more aspects of the vessel, or as an alternate, the mixing vessel further includes a third segment, wherein the third segment is the insulator, metal, or alloy different than the first segment and the second segment.

In addition to one or more aspects of the vessel, or as an alternate, the first segment is a first arm and the second segment is a second arm that are diagonally disposed to each other, wherein the first arm has a first upper end and a first lower end and the second aim has a second upper end and a second lower end.

In addition to one or more aspects of the vessel, or as an alternate, the first and second arms are connected in communicating relation with each other at the first and second lower ends; the first arm and the second arm diverge upwardly from the first and second lower ends; the first and second upper ends are open; and first and second closures are configured for removable positioned within the first and second upper ends for selectively closing the first and second upper ends of the first and second arms.

In addition to one or more aspects of the vessel, or as an alternate, the mixing vessel is a V-shaped blender, a cylindrical blender, a double cone blender, a tote blender or a bin blender.

In addition to one or more aspects of the vessel, or as an alternate, the first arm is included of the first segment and the second arm is included of the second segment.

In addition to one or more aspects of the vessel, or as an alternate, the first and second arm include a combination of the first segment and the second segment.

In addition to one or more aspects of the vessel, or as an alternate, the first and second aim include a plurality of stripes including the first segment and the second segment, wherein adjacent stripes include different segments.

Further disclosed is powder mixing device, including: a stand; a frame mounted to the stand, the frame being rotatable around a first axis of rotation; and a mixing vessel having one or more of the aspects disclosed herein mounted to the frame, the mixing vessel being rotatable around the first axis of rotation; and a motor configured to rotate the frame.

In addition to one or more aspects of the device, or as an alternate, the mixing vessel is a V-shaped blender, a cylindrical blender, a double cone blender, a tote blender or a bin blender.

Further disclosed is a method for mixing powders, the method including: providing a powder to be mixed, wherein the powder includes one or more active pharmaceutical ingredient, and the powder has a particle size of between 1 μm and 5000 μm; loading the powder into a vessel or a mixing device having one or more of the aspects disclosed herein; and admixing the powder, thereby producing a powder with a charge lower than the powder mixed in a mixing device with a single component mixing vessel.

In addition to one or more aspects of the method, or as an alternate, the method includes maintaining a temperature range of about 68-77 F and a relative humidity of about 30-40%.

In addition to one or more aspects of the method, or as an alternate, the powder includes acetaminophen, albuterol, piracetam, cetirizine, levetiracetam, lacosamide, levocetirizine, rotigotine, adenosine, ascorbic acid, alprostadil, amiodarone HCl, amitriptyline HCl, amlodipine besylate, ampicillin, anastrozole, apomorphine, atropine sulfate, baclofen, benzocaine, betadine, betamethasone, biotin, bromfenac, brompheniramine, budesonide, bumetanide, bupivacaine HCl, buprenorphine HCl, caffeine citrate, calcifediol, calcium gluconate, carbamazepine, cefazolin sodium, cefepime, ceftazidime, ceftriaxone sodium, cefuroxime, choline chloride, cidofovir, cephalosporin (7-aminocephalosperanic acid), ciprofloxacin, clindamycin phosphate, clonidine HCl, cyanocobalamin, cyclobenzaprine HCl, cyclosporine, cyclopentolate HCl, dehydroepianodrosterone, demercarium bromide, dexamethasone acetate, dexamethasone phosphate, dexmedetomidine, dextromethorphan hydrobromide, diazepam, diclofenac sodium, diltiazem and its salts, diphenhydramine HCl, dipyridamole, dobutamine, dopamine HCl, doxepin HCl, doxycycline, droperidol, ectoine, edetate disodium, edetate calcium disodium, ephedrine sulfate, epinephrine bitartate, estradiol, estriol, estrone, erythritol, fenbendazole, fentanyl citrate, finasteride, furosemide, gabapentin, gatifloxacin, gentamicin sulfate, glutathione, glycopyrrolate, guaifenesin, hydrocortisone and its salts, hydromorphone HCl, hydroxocobalamin HCl, hydroxyprogesterone caproate, ibuprofen, idoxuridine, inositol, isoproterenol, ketamine HCl, ketoprofen, ketorolac tromethamine, labetalol HCl, leuprolide acetate, levothyroxine sodium, lidocaine HCl, liothyronine sodium, lorazepam, medroxyprogestone acetate, meloxicam, meperidine HCl, methadone HCl, methionine, methocarbamol, methohexital sodium, methylcobalamin, methylprednisolone and its salts, metoclopramide HCl, metoprolol, midazolam HCl, milrinone, minoxidil, mitomycin, mometasone furoate, morphine sulfate, moxifloxacin HCl, N-acetylcysteine, nalbuphine HCl, naltrexone HCl, nandrolone decanoate, neostigmine methylsulfate, nicardipine HCl, nifedipine, nitroglycerin, norepinephrine bitartrate, omeprazole sodium, ondansetron, orphenadrine citrate, oseltamivir, oxymetaioline, oxytocin, pregabalin, rifampicin, shikimic acid, succinic acid, theophylline, pantoprazole, pentobarbital, phenylephrine, piroxicam, ranitidine, ropivacaine, tacrolimus, thiamine, tramadol, triamcinolone, vancomycin, verapamil, tropicamide, lactose monohydrate, D-mannitol, or cellulose.

BRIEF DESCRIPTION OF THE DRAWINGS

Reference will now be made to the accompanying drawings, which are not necessarily drawn to scale, and wherein:

FIG. 18A shows the unrecovered powder in the aluminum (Al) blender.

FIG. 18B1 shows the unrecovered powder in the PVC arm of the Al-PVC blender.

FIG. 18B2 shows the unrecovered powder in the Al arm of the Al-PVC blender.

FIG. 18C shows the unrecovered powder in the PVC blender.

FIG. 18D shows the unrecovered powder in the stainless-steel (SS) blender.

FIG. 18E1 shows the unrecovered powder in the PVC arm of the SS-PVC blender. FIG. 18E2 shows the unrecovered powder in the SS arm of the SS-PVC blender.

DETAILED DESCRIPTION

Triboelectrification being one of the primary reasons of dust explosions in particulate industry, necessitates an option to reduce charge generation during dynamic processes. Techniques implemented in the industry, often fail to mitigate charging. Stop-gap reforms are often implemented, or the processing techniques are modulated to accommodate such charge accumulation, without full proof risk mitigation. The disclosed embodiments reduce these dust explosions thereby increasing the occupational safety. Pharmaceutical powders are mixed (or blended) with excipients during manufacturing in particular amounts can lead to decrease in Tribocharging. However, it is required to use large amounts of excipients which could lead to high cost of manufacturing and there is always a risk of drug-excipient incompatibilities. It is also known that toxicity of excipients is different in pediatric population and therefore, it is important to perform toxicity studies in different patient populations which further requires time and money. Equipment grounding is a common practice to reduce electrostatic charging during powder processing, but as pharmaceutical materials are insulators with low conductivity ($10^{-12}$ S/cm) relative to metals ($10^{7}$ S/cm), this practice is not very efficient for insulator powders.

The disclosed embodiments target to mitigate tribocharging in powders encountered during blending or mixing process. APIs (active pharmaceutical ingredients) have low solubility leading to low dissolution rates which necessitates that they are milled or micronized to improve dissolution. During micronization APIs gets extensively charged. The charging of different powders could result from ion, electron or material transfer. However, it is difficult to predict the mechanism responsible for charging of pharmaceutical powders as most of them are insulators and they do not possess free electrons to release. Thus, the insulator surfaces often maintain abundance of charges created by tribocharging. A powder mixing device is fabricated using a combination of insulator and metal (with significantly different work functions) materials which demonstrated significant reduction in charge of the powder being blended. The blender can be of any suitable size and shape, for example as shown in FIGS. 19A-19E, a V-shaped blender 110, a cylindrical blender 110, a double cone blender 110, a tote blender 110 or bin blender 110. In the illustrated embodiments, the blender 110 is a V-shaped blender. The blenders have support frames 111 and controllers 112 that are typically utilized for supporting and controlling the blenders 110.

Figure 1:
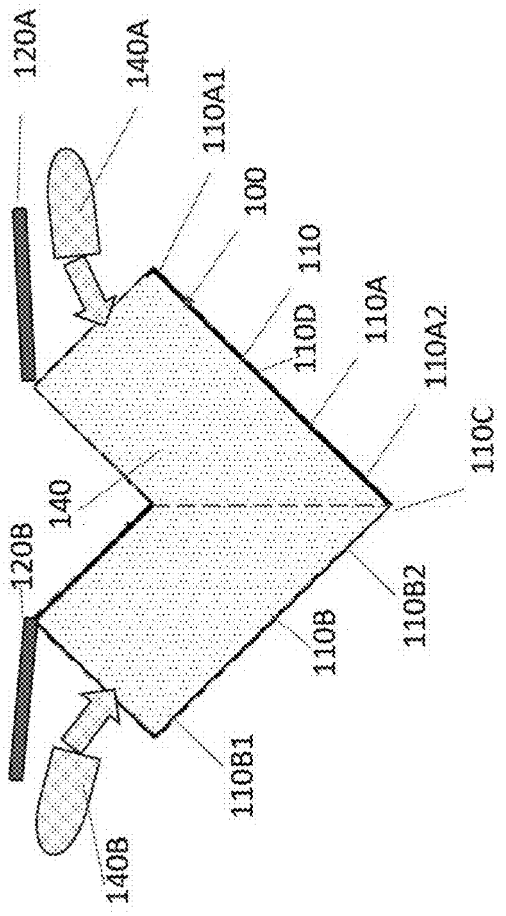
FIG. 1 shows a schematic representation of a V-shaped Blender.

Turning to FIG. 1, in certain embodiments, the powder mixing system 100 (FIG. 9) includes a V-shaped container (for simplicity, a container 110) having diagonally disposed first and second cylindrical arms (for simplicity, first and second arms) 110A, 110B, generally referred to as arms 110A, 110B. The first and second arms 110A, 110B are also referred to herein as first and second segments or components of the container 110.

The first arm 110A has first upper and lower ends 110A1, 110A2 and the second arm has second upper and lower ends 110B1, 110B2. The first and second lower ends 110A2, 110B2 are connected to each other at a vertex 110C of the container 110 to form a continuous passage 110D between the first and second upper ends 110A1, 110B1 of the container 110. The arms 110A, 110B diverge upwardly from the first and second lower ends 110A2, 110B2, at the vertex 110C, where the arms 110A, 110B are connected in communicating relation with each other. The first and second upper ends 110A1, 110B1 of the arms 110A, 110B are open. First and second closures or end caps 120A, 120B, generally referred to as 120, are provided for the open first and second upper ends 110A1, 110B1 of the arms 110A, 110B. The closures 120 are selectively insertable and removable, into and out of closing relation with the arms 110A, 110B, to fluidly seal the arms 110A, 110B and the passage 110D. As shown in FIG. 1, the container 110 is V-shaped, and may alternatively be referred to as a V-shaped blender or V-blender or mixing vessel.

Any suitable insulator and metal or alloy can be used to fabricate the container 110. Nonlimiting examples for insulators are polymethyl methacrylate (PMMA), polyvinyl chloride (PVC), nylon, polytetrafluoroethylene (Teflon), or a combination thereof. Nonlimiting examples for metals or alloys are Aluminum, stainless steel, or a combination thereof.

Figure 2:
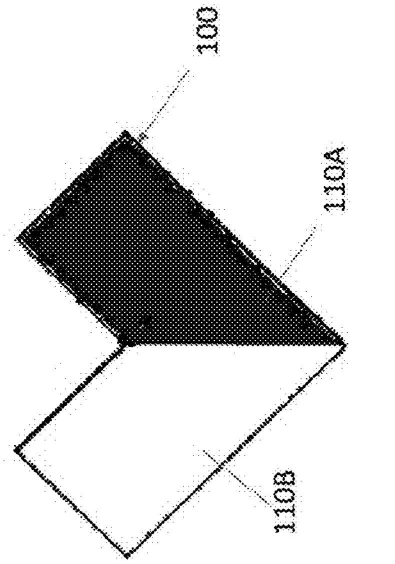
FIG. 2 shows a schematic representation of a V-shaped Blender with each arm made from different component.
Figure 3:
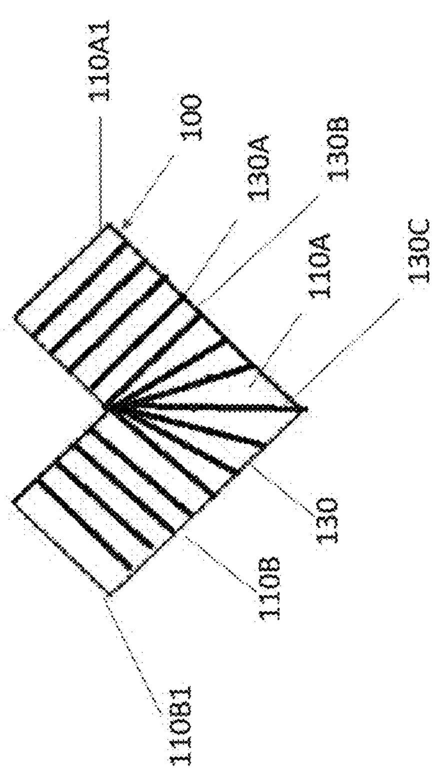
FIG. 3 shows a schematic representation of a zebra stripe V-shaped Blender with zebra stripes of different components, wherein each stripe represents a different component than the adjacent component.

As shown in FIG. 2, the first and second arms 110A, 110B of the container 100 may be formed from different materials. As shown in FIG. 3, the arms 110A, 110B of the container 110 each may be formed of layers 130, e.g., first and second layers 130A, 130B, that are each full hoop segments that alternate, one after another, between the upper ends 110A1, 110B1 of the container 110. One of the layers 130 may be axially (along the axial direction of each of the arms 110A, 110B) longer than the other one of the layers 130. Each layer 130 may be formed of a different material so that the container 110 is formed of a mixture of two materials.

It is to be appreciated that additional layers 130 or hoop segments of differing materials may be included, for example a third material layer 130C may be included as one of the repeating sequences of hoops or may be located at a predetermined position along the container 110, such as the vertex 110C, so that the layers 130 form a repeating, or a non-repeating pattern. For example, the layers 130 of the container 110 may form a plurality of stripes and for example, zebra stripes, where each stripe represents a different material than the adjacent stripe. The third material layer 130C, otherwise referred to as a third segment or component, may be the insulator, metal, or alloy different than the first segment 110A and the second segment 110B. It is to be appreciated one or more of the hoops, when formed as zebra stripes, may form partial hoops rather than continuous hoops.

As shown in FIG. 1, the container 110 may be utilized to blend materials or powders, generally referenced as 140, such as first and second powders 140A, 140B that have been poured into the first and second upper ends 120A, 120B prior to closing the container 110 with the end caps 120A, 120B. The powders 140 may have the same or different size as each other. Powders 140 of different particle sizes can be utilized. For example, powders 140 with the particle size of about 1 μto about 5000 μm, about 1 μm to about 4000 μm, about 1 μm to about 3000 μm, about 1 μm to about 2000 μm, about 1 μm to about 1000 μm, about 1 μm to about 500 μm, about 100 μm to about 1000 μm, or about 100 μm to about 500 μm, can be used.

The V-blender 110 can help in decreasing tribocharging by inducing opposite polarity of charges on the same powder 140 during processing in the blender 110. The arm 110A made of metal of the blender 110 induces charge on powder 140 that is opposite in polarity to that induced by the arm 110B made of insulator material such as polyvinyl chloride (PVC). The induced charge will be neutralized when particles of powder 140 of opposite polarity interact with each other during tumbling motion as mixing progresses. In certain embodiments, the first arm 110A of the V-blender 110 includes is formed of an insulating material and the second arm 110B is formed of a metal or an alloy (FIG. 2). In certain embodiments, each of the arms 110A, 110B includes a combination of an insulator, a metal, and/or alloy (FIG. 3).

Figure 9A:
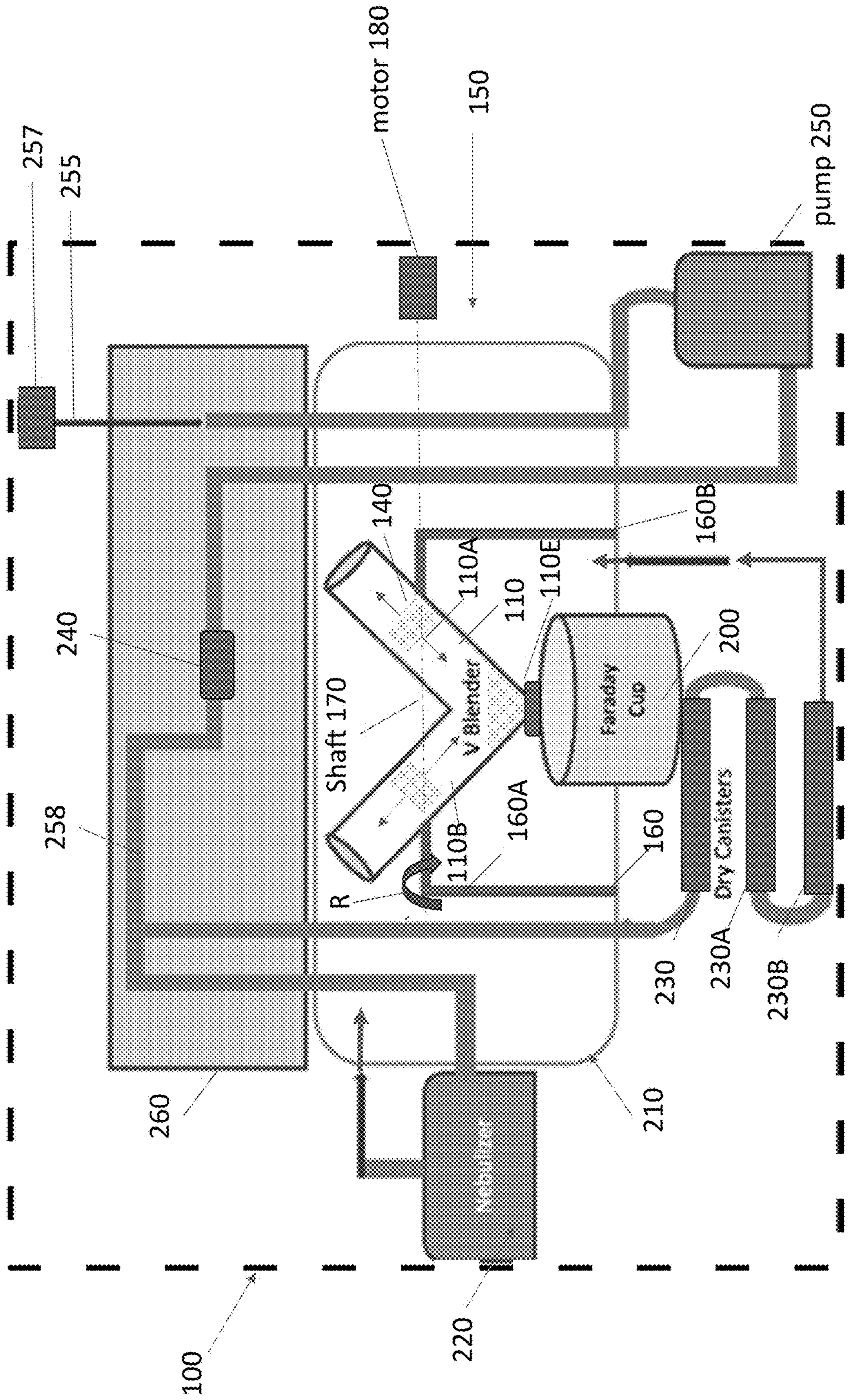
FIG. 9A shows a V-blender assembly inside humidity-controlled chamber used to perform experiments.

Turning to FIG. 9A, the system 100 includes powder mixing device 150. The mixing device 150 includes a stand 160 which may include first and second stand members 160A, 160B. A frame 170 is mounted to the stand 160. The frame 170 may be a shaft. A motor 180 to rotate the shaft 170 around a first axis of rotation R. The container 110 is mounted to the shaft 170 to rotate around the first axis of rotation R.

More specifically, the system 100 may be a blender assembly. The system 100 may include an enclosure 210. The container 110 may have a removable lower end cap 110E. The powder mixing device 150 may be within the enclosure 210. A Faraday cup 200 may he within the enclosure 210 configured to receive mixed powder from the container 110 by removal of the lower end cap 110E. The Faraday cup 200 may be utilized to test the charge in the powder 140 to confirm it is within an acceptable range, i.e., one that does not result to clinging to the surface, of the blender 110. The Faraday cup 200 is optional. The system 100 may have a nebulizer 220 configured to inject moisture into the enclosure 210 to control humidity. One or more dry canisters 230A, 230B (generally referenced as 230) may be operationally coupled to the enclosure 210 and configured to remove moisture from the enclosure 210, also to control humidity. In the pharmaceutical industry one would use a cGMP (Current Good Manufacturing Practice) cleanroom facility to process powders. A GMP facility will have temperature ranging 68-77 F and relative humidity around 30-40%.

The system 100 may include a pump 250 that pumps fluid 255 from a remote chamber 257 to the nebulizer 220 via conduits 258 to the canisters 230 as needed to control humidity. A pressure gauge 240 within the conduits 258 may monitor pressure acting on the nebulizer 220 confirm pressure remains below a threshold. A control panel 260 is operationally coupled to the nebulizer 220, the pump 250 the Faraday cup 200, the motor 180 and the pressure gauge 240. The control panel 260 controls operation of the blender 110, the humidity level within the enclosure 210, determines the charge induced in mixed powder 140 via the Faraday cup 200 and modulates operation of the pump 250 to maintain a predetermined pressure in the conduits 258.

According to an embodiment, the first segment 110A has a first work function (i.e., the property of a material that measures the minimum energy needed to remove an electron from a solid surface) higher or lower than a second work function of the second segment 110B, and a third work function of the powder 140 to be mixed is within the work function of the first segment 110A and the second segment 110B. In certain embodiments, the components of the mixing vessel 110 are selected based on the work function of the powder 140 to be mixed. In certain embodiments, the first segment 110A has the work function higher than the work function of the powder 140 to be mixed and the second segment 110B has the work function lower than the work function of the powder 140 to be mixed. In certain embodiments, the first segment 110A has the work function lower than the work function of the powder 140 to be mixed and the second segment 110B has the work function higher than the work function of the powder 140 to be mixed. Due to the difference in work functions, a charge will be induced in the particles of powder 140 in one arm 110A that is the opposite to the charge induced in the other arm 110B. As a result, the charge will be neutralized when particles of powder 140 of opposite polarity interact with each other during tumbling motion as mixing progresses.

In certain embodiments, the first segment 110A has a work function significantly higher or lower than a work function of the second segment 110B, and a work function of a powder 140 to be mixed is within the work function of the first segment 110A and the second segment 110B. As used herein "significantly higher or lower" means that the work function is at least 1.5 times to 100 times higher or lower, for example about 1.5 times, 2 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times, 10 times, 20 times, 30 times, 40 times, 50 times, 60 times, 70 times, 80 times, 90 times, or 100 times higher or lower than the work function of another component.

In certain embodiments, the higher work function is about 4 eV (electronvolt) to about 10 eV and the lower work function is about 1 eV to about 4 eV. In certain embodiments, the higher work function is about 6.01 eV and the lower work function is about 3.93 eV. In certain embodiments, the first segment 110A has the work function about 6.01 eV and the second segment 110B has the work function about 3.93 eV. In certain embodiments, the first segment 110A has the work function about 3.93 eV and the second segment 110B has the work function about 6.01 eV.

In certain embodiments, the first segment 110A is an insulator. In certain embodiments, the first segment 110A includes polymethyl methacrylate (PMMA), polyvinyl chloride (PVC), nylon, polytetrafluoroethylene (Teflon), or a combination thereof.

In certain embodiments, the second segment 110B is a metal or an alloy. In certain embodiments, the second segment 110B includes Aluminum, stainless steel, or a combination thereof.

Figure 9B:
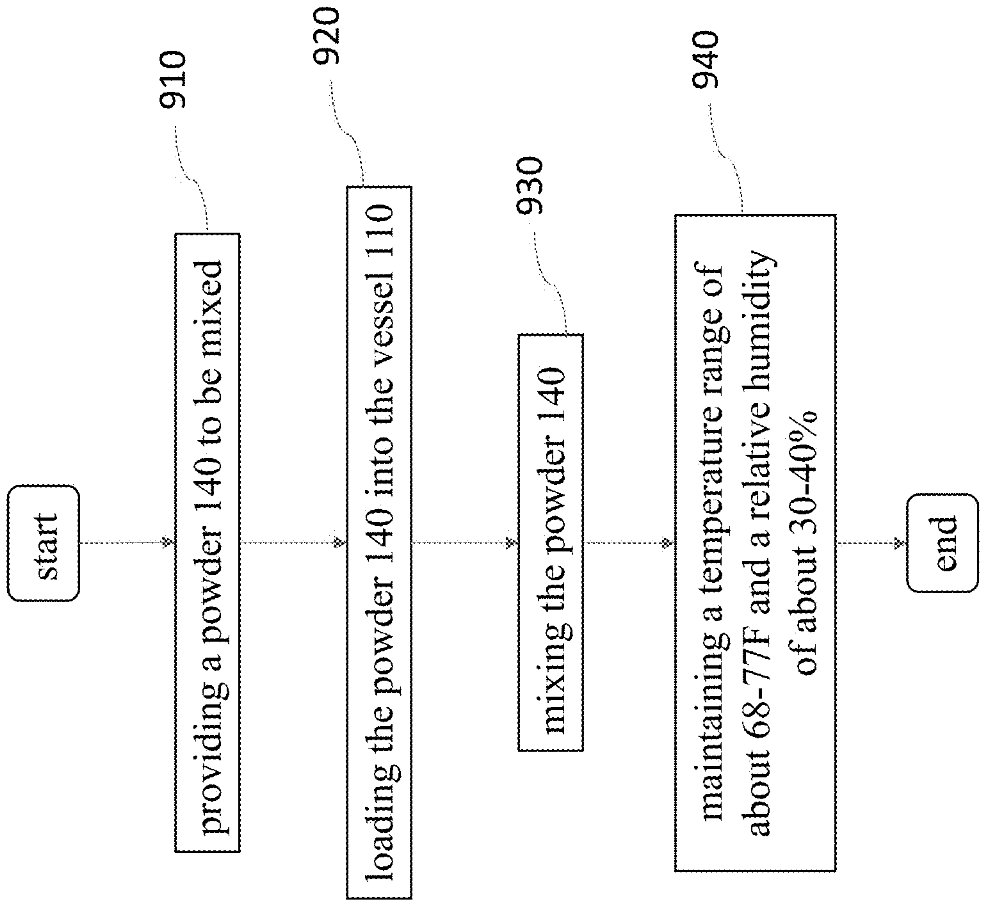
FIG. 9B is a flowchart showing a method of mixing powder according to an embodiment.

As shown in FIG. 9B, in an aspect, disclosed is a method for mixing powders 140. As shown in block 910, the method includes providing a powder 140 to be mixed. As shown in block 920, the method includes loading the powder 140 into the vessel 110 that may be part of the powder mixing device 150 or the system 100. As shown in block 930, the method includes mixing the powder 140. In certain embodiments, the powder 140 includes one or more active pharmaceutical ingredient (API). As shown in block 940, the method includes maintaining a temperature range of about 68-77 F and a relative humidity of about 30-40%. For example, the method includes maintaining the temperature range of about 68-76 F, 68-75 F, 68-74 F, 68-73 F, 68-72 F, 68-71 F, 68-70 F, or about 68-69 F. As a further example, the method includes maintaining the relative humidity of about 30-32%, 30-34%, 30-36%, or about 30-38%.

The nonlimiting examples for APIs are acetaminophen, albuterol, piracetam, cetirizine, levetiracetam, lacosamide, levocetrizine, rotigotine, adenosine, ascorbic acid, alprostadil, amiodarone HCl, amitriptyline HCl, amlodipine besylate, ampicillin, anastrozole, apomorphine, atropine sulfate, baclofen, benzocaine, betadine, betamethasone, biotin, bromfenac, brompheniramine, budesonide, bumetanide, bupivacaine HCl, buprenorphine HCl, caffeine citrate, calcifediol, calcium gluconate, carbamazepine, cefazolin sodium, cefepime, ceftazidime, ceftriaxone sodium, cefuroxime, choline chloride, cidofovir, cephalosporin (7-aminocephalosperanic acid), ciprofloxacin, clindamycin phosphate, clonidine HCl, cyanocobalamin, cyclobenzaprine HCl, cyclosporine, cyclopentolate HCl, dehydroepianodrosterone, demercarium bromide, dexamethasone acetate, dexamethasone phosphate, dexmedetomidine, dextromethorphan hydrobromide, diazepam, diclofenac sodium, diltiazem and its salts, diphenhydramine HCl, dipyridamole, dobutamine, dopamine HCl, doxepin HCl, doxycycline, droperidol, ectoine, edetate disodium, edetate calcium disodium, ephedrine sulfate, epinephrine bitartate, estradiol, estriol, estrone, erythritol, fenbendazole, fentanyl citrate, finasteride, furosemide, gabapentin, gatifloxacin, gentamicin sulfate, glutathione, glycopyrrolate, guaifenesin, hydrocortisone and its salts, hydromorphone HCl, hydroxocobalamin HCl, hydroxyprogesterone caproate, ibuprofen, idoxuridine, inositol, isoproterenol, ketamine HCl, ketoprofen, ketorolac tromethamine, labetalol HCl, leuprolide acetate, levothyroxine sodium, lidocaine HCl, liothyronine sodium, lorazepam, medroxyprogestone acetate, meloxicam, meperidine HCl, methadone HCl, methionine, methocarbamol, methohexital sodium, methylcobalamin, methylprednisolone and its salts, metoclopramide HCl, metoprolol, midazolam HCl, milrinone, minoxidil, mitomycin, mometasone furoate, morphine sulfate, moxifloxacin HCl, N-acetylcysteine, nalbuphine HCl, naltrexone HCl, nandrolone decanoate, neostigmine methylsulfate, nicardipine HCl, nifedipine, nitroglycerin, norepinephrine bitartrate, omeprazole sodium, ondansetron, orphenadrine citrate, oseltamivir, oxymetazoline, oxytocin, pregabalin, rifampicin, shikimic acid, succinic acid, theophylline, pantoprazole, pentobarbital, phenylephrine, piroxicam, ranitidine, ropivacaine, tacrolimus, thiamine, tramadol, triamcinolone, vancomycin, verapamil, tropicamide, lactose monohydrate, D-mannitol, cellulose, and a combination thereof.

In certain embodiments, the powder 140 has a particle size of about 1 μm to about 5000 μm. In certain embodiments, the powder includes ibuprofen, acetaminophen, theophylline, lactose monohydrate, cellulose, or a combination thereof. In certain embodiments, the method produces a powder with a charge lower than the powder mixed in a mixing device with a single component mixing vessel.

The disclosed blender 110 can be used in pharmaceutical industry to improve the mixing performance thereby preventing segregation of drug particles leading to blend homogeneity which improves drug content uniformity as there are strict compendial limits on dose content uniformity in pharmaceuticals. The disclosed blender 110 can be used to improve the mixing of materials by preventing sticking of material particles to the blender. This will reduce losses and improve recovery of the blended materials.

The use of disclosed blender 110 can reduce tribocharging of powders or granular materials which will decrease the risk of fire explosions due to electrostatic charging and discharging.

The use of disclosed embodiments could be extended to other industries such as food, mining, agriculture, ceramics, polymer, defense, automotive and printing where tribocharging is often a problem. The blender can be used as disposable equipment to avoid recalls due to batch-to-batch contamination, long cleaning procedures and labor costs. Disclosed V-shaped blender can improve content uniformity in pharmaceutical dosage forms leading to decreased chances of drug recalls and thereby more economical for the company.

Triboelectrification being one of the primary reasons of dust explosions in particulate industry, necessitates an option to reduce charge generation during dynamic processes. Techniques implemented in the industry, often fails to mitigate charging. Stop-gap reforms are often implemented, or the processing techniques are modulated to accommodate such charge accumulation, without full proof risk mitigation. The disclosed embodiments can help in reducing these dust explosions thereby increasing the occupational safety.

Tumble blenders as disclosed herein, such as V-blenders and double-cone blenders mix particles by tumbling. The particles roll, collide and interact with each other and the vessel surface as the vessel rotates on a horizontal axis. In a V-blender, the batch is continuously split and recombined across the two sides of the vessel as the vessel rotates.

The blenders and methods described herein are particularly useful for blending active pharmaceutical ingredients. The blenders and methods described herein can reduce sticking and loss of active pharmaceutical ingredients during blending. As used herein, an "active ingredient" refers to one or more substances belonging to any of the following categories: API (active pharmaceutical ingredient), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods." These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Active ingredients are typically blended with excipients in the preparation of pharmaceutical formulations. As used herein, an "excipient" is an inactive ingredient in a pharmaceutical formulation. Examples of excipients include fillers or diluents, surfactants, binders, glidants, lubricants, disintegrants, and the like.

As used herein, a blender or mixing device is a laboratory appliance used to mix substances including but not limited to powders.

As used herein, a "disintegrant" is an excipient that hydrates a pharmaceutical formulation and aids in tablet dispersion. Examples of disintegrants include sodium croscarmellose and/or sodium starch glycolate.

As used herein, a "diluent" or "filler" is an excipient that adds bulkiness to a pharmaceutical formulation. Examples of fillers include lactose, sorbitol, celluloses, calcium phosphates, starches, sugars (e.g., mannitol, sucrose, or the like) or any combination thereof.

As used herein, a "surfactant" is an excipient that imparts pharmaceutical formulations with enhanced solubility and/or wetability. Examples of surfactants include sodium lauryl sulfate (SLS), sodium stearyl fumarate (SSF), polyoxyethylene 20 sorbitan mono-oleate (e.g., Tween™), or any combination thereof.

As used herein, a "binder" is an excipient that imparts a pharmaceutical formulation with enhanced cohesion or tensile strength (e.g., hardness). Examples of binders include dibasic calcium phosphate, sucrose, corn (maize) starch, microcrystalline cellulose, and modified cellulose (e.g., hydroxymethyl cellulose).

As used herein, a "glidant" is an excipient that imparts a pharmaceutical formulation with enhanced flow properties. Examples of glidants include colloidal silica and/or talc.

As used herein, a "colorant" is an excipient that imparts a pharmaceutical formulation with a desired color. Examples of colorants include commercially available pigments such as FD&C Blue #1 Aluminum Lake, FD&C Blue #2, other FD&C Blue colors, titanium dioxide, iron oxide, and/or combinations thereof.

As used herein, a "lubricant" is an excipient that is added to pharmaceutical formulation, particularly those that are pressed into tablets. The lubricant aids in compaction of granules into tablets and ejection of a tablet of a pharmaceutical formulation from a die press. Examples of lubricants include magnesium stearate, stearic acid (stearin), hydrogenated oil, sodium stearyl fumarate, or any combination thereof.

Blends including pharmaceutical active agents can then be processed, such as by granulation, and/or configured for oral use in various forms, including gels, pastilles, gums, chews, melts, tablets, lozenges, powders, and pouches.

The compositions can be formed into a variety of shapes, including pills, tablets, spheres, strips, films, sheets, coins, cubes, beads, ovoids, obloids, cylinders, bean-shaped, sticks, or rods. Cross-sectional shapes of the composition can vary, and example cross-sectional shapes include circles, squares, ovals, rectangles, and the like. Such shapes can be formed in a variety of manners using equipment such as moving belts, nips, extruders, granulation devices, compaction devices, and the like.

EXAMPLES

Figure 4:
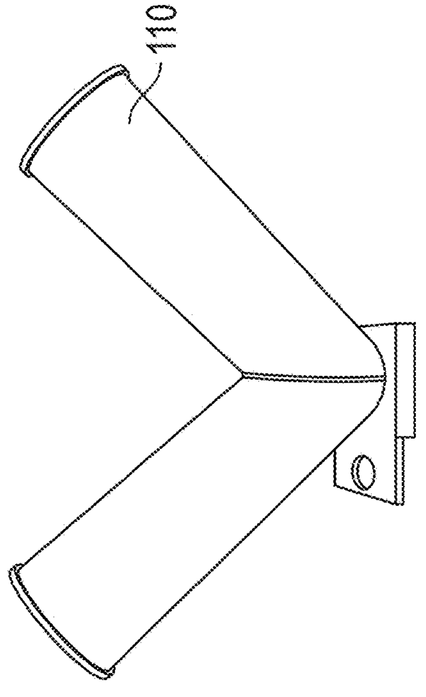
FIG. 4 (Prior Art)
FIG. 4 shows a known Aluminum blender.
Figure 5:
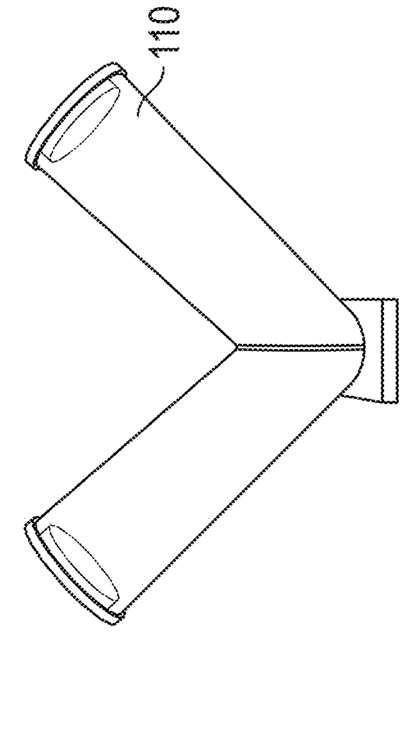
FIG. 5 (Prior Art)
FIG. 5 shows a known PVC blender.
Figure 6:
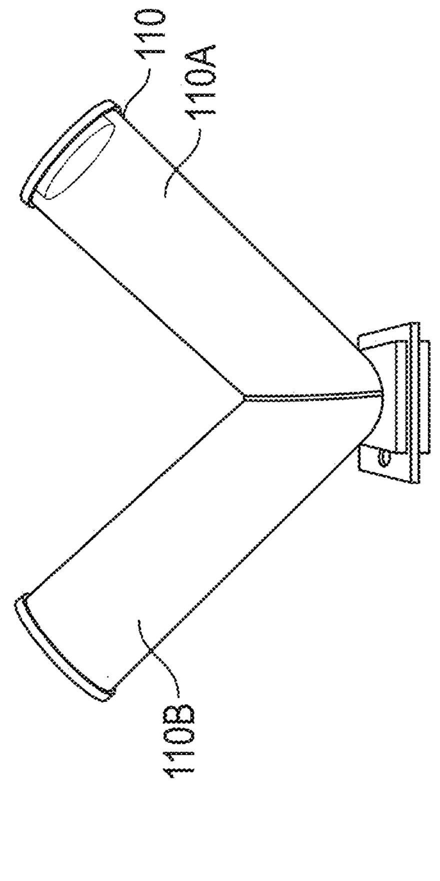
FIG. 6 shows a blender with Aluminum and PVC (Al-PVC) arm.

The studies were performed using Aluminum blender 110 (FIG. 4), a PVC blender 110 (FIG. 5), a V blender 110 fabricated by using Aluminum for one arm 110A and PVC for another arm 110B (Al-PVC) (FIG. 6). The Aluminum arm and Polyvinyl chloride arm were expected to induce charge of opposite polarity on the powder leading to charge neutralization by tumbling motion during blending.

Figure 7:
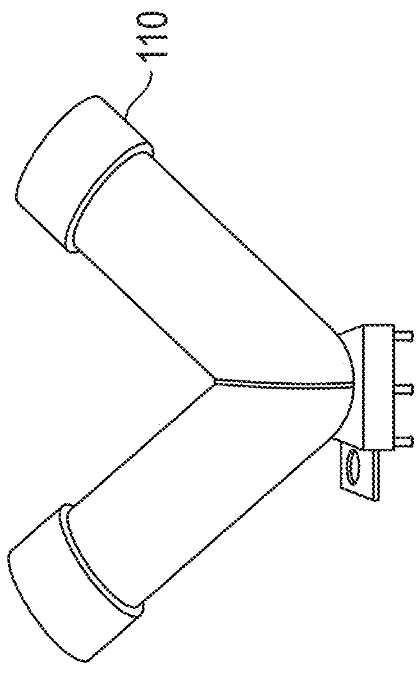
FIG. 7 (Prior Art)
FIG. 7 shows a known Stainless-steel blender.
Figure 8:
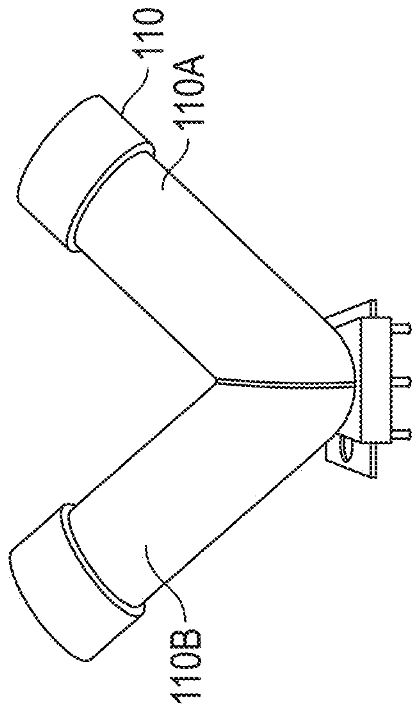
FIG. 8 shows a blender with Stainless-steel and PVC arm.

Additional electrostatic charging studies were performed with Current Good Manufacturing Practice Regulations (cGMP) materials (stainless steel and PVC) and three blenders 110 were fabricated as Stainless-steel blender 110 (FIG. 7), a PVC blender 110 (FIG. 5) and a blender 110 with a PVC arm 110A and a stainless steel arm 110B (SS-PVC) (FIG. 8).

Experimental Methodology:

Ibuprofen was chosen as the model blending powder 140 due to its ability to charge excessively and was evaluated in all the V blenders 110. The V blender materials were procured from McMaster-Carr (https://www.mcmaster-.com/) and was fabricated at the University of Connecticut (https://uconn.edu/). Ibuprofen powder 140 was spread into thin layers onto aluminum foil and equilibrated overnight at 16% RH along with the V blender 110 before the blending experiments. Before starting the experiment, initial charge was measured using Faraday cup 200. The blender 110 was charged with the powder 140 and blended in all the blenders for different time intervals. After completion of the tribocharging experiment powder was collected in the Faraday cup 200 connected to a nano-coulombmeter to measure the charge, which was reported as charge to mass ratio, also known as specific charge (nC/g) (FIG. 9). All experiments were done in triplicate at room temperature and at 16% RH. Similar experiments were also performed using ibuprofen—excipient blends to understand equipment capability to mitigate electrostatic charging in other powders. For this study, Ibuprofen—Sugar sphere (500/600 μm) blends were evaluated using stainless steel (SS), stainless steel-PVC (SS-PVC), and PVC blenders. Sugar spheres is widely used excipient for sustained-release pellet formulations used in oral dosage forms therefore, selected for this study.

Example 1

Effect of Contact Surface on the Triboelectrification (Ibuprofen Only)

Figure 10:
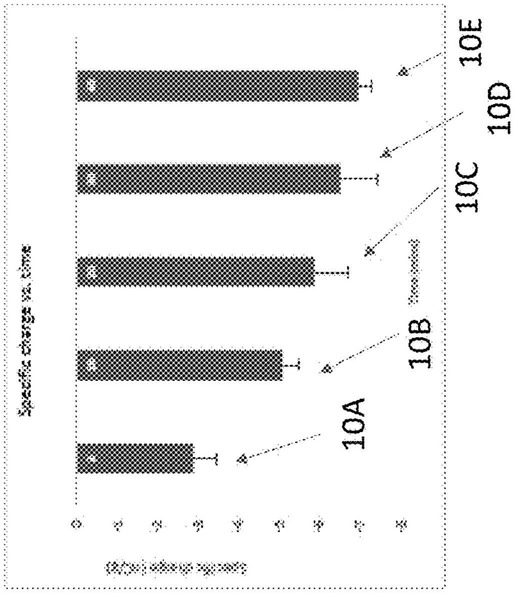
FIG. 10 shows Specific charge (nC/g) acquired by ibuprofen using Aluminum blender.
Figure 11:
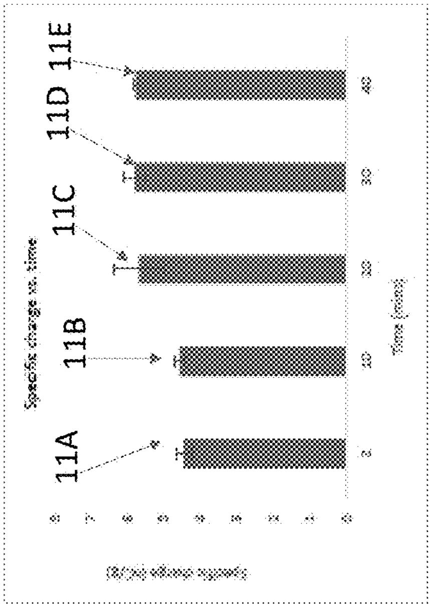
FIG. 11 shows specific charge (nC/g) acquired by ibuprofen using PVC blender.
Figure 12:
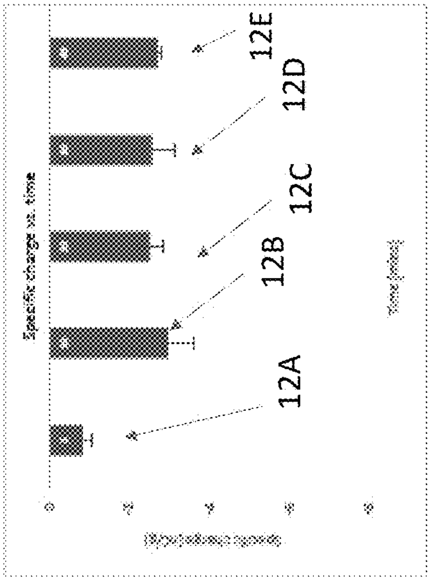
FIG. 12 shows specific charge (nC/g) acquired by ibuprofen using Al-PVC blender.

With reference to FIGS. 10-16, to study triboelectrification, a measured quantity 50 g of ibuprofen was loaded into the V blender 110 which were rotated at 13 rpm for different time intervals. The experiments were performed for different time intervals such as 2, 10, 20, 30, and 40 mins (respectively graphed as bars A-E in FIGS. 10-14) at 13 rpm and 16% relative humidity. Ibuprofen was found to charge negatively with Aluminum blender 110 of FIG. 4 as shown with the different graphed bars 10A-10E of the bar graph of FIG. 10 and positively with the PVC blender 110 of FIG. 5 as shown with the different graphed bars 11A-11E of the bar graph of FIG. 11. The charge saturation was observed at 30 mins and no significant variation in charge was noted after 30 mins. The charge accumulated with a blender 110 (FIG. 6) was significantly less than the PVC and Al blender 110 of FIG. 6. Final charge with Al-PVC blender 110 of FIG. 6 as shown with the different graphed bars 12A-12E of the bar graph of FIG. 12 was negative in polarity, e.g., due to more interaction of ibuprofen with Aluminum. It can be observed after comparing specific charge from three blenders 110, the Al-PVC blender 110 of FIG. 6 can reduce charge (FIGS. 10-12).

Figure 13:
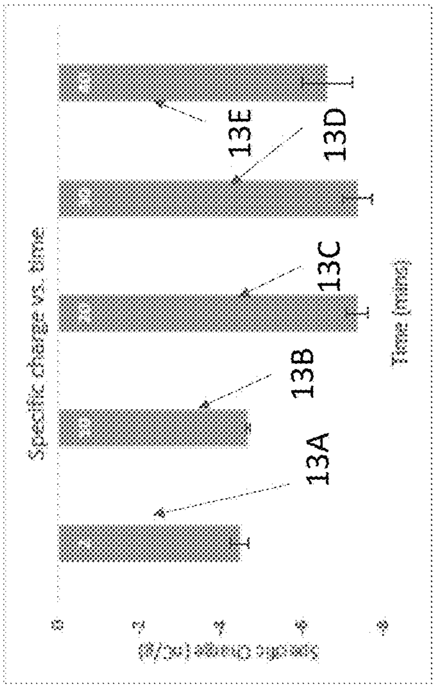
FIG. 13 shows specific charge (nC/g) acquired by ibuprofen using Stainless steel blender.
Figure 14:
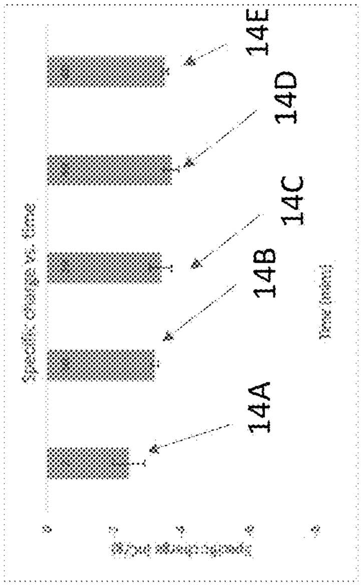
FIG. 14 shows specific charge (nC/g) acquired by ibuprofen using a SS-PVC blender.
Figure 15:
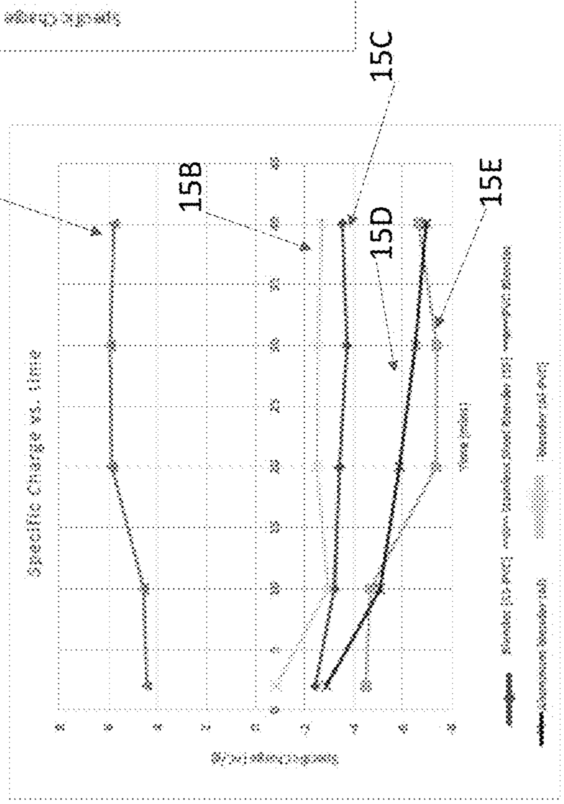
FIG. 15 shows the comparison of specific charge (nC/g) acquired by ibuprofen for all five blenders.
Figure 16:
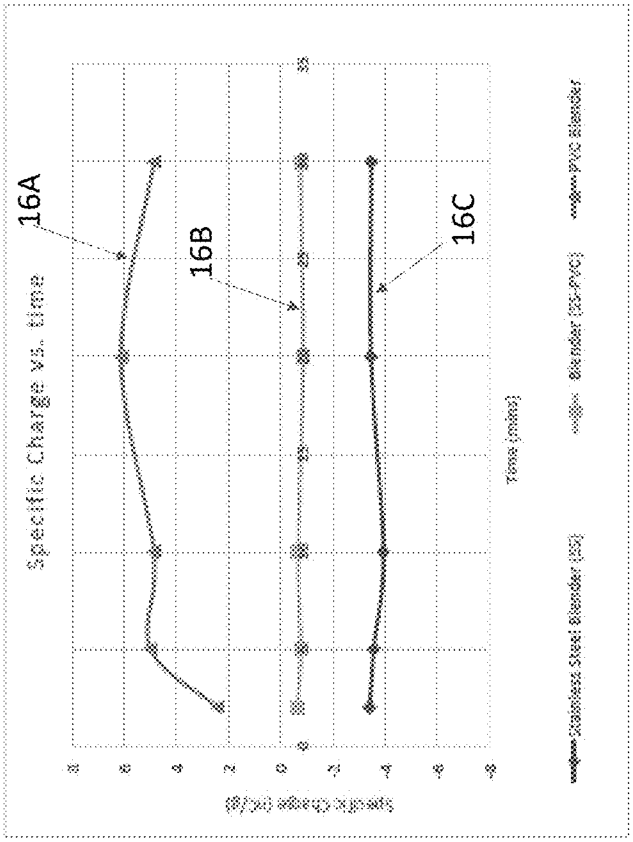
FIG. 16 shows the comparison of specific charge (nC/g) acquired by ibuprofen—sugar spheres (500/600 μm) for three cGMP blenders.

The electrostatic charging studies were performed with blenders fabricated using cGMP FDA approved materials, it was observed that ibuprofen attained negative charge with stainless steel blender 110 of FIG. 7 as shown with the different graphed bars 13A-13E of the bar graph of FIG. 13, positive charge with the PVC blender 110 of FIG. 5 as shown with the different graphed bars 14A-14E of the bar graph of FIG. 14 and negative charge with the stainless steel and PVC blender (SS-PVC) of FIG. 8 as shown with the different graphed lines 15A-15E in the line graph of FIG. 15, and specifically line 15E. Additionally, the graphs of these FIGS. are showing the charge in nC/g which might appear small but industrial manufacturing involves large scale handling of powders which leads to huge electrostatic charging.

Example 2

Effect of Contact Surface on the Triboelectrification (Ibuprofen—Sugar Sphere Blends)

To perform this study, similar experimental plan was followed as for ibuprofen only experimentation using Ibuprofen and sugar spheres in 70:30 ratio. The powder mixture charged negatively with stainless steel blender 110 of FIG. 7 and the SS-PVC blender 110 of FIG. 8, but positively with PVC blender 110 of FIG. 5. It was observed that specific charge decreased significantly with the SS-PVC blender of FIG. 7 as shown with the different graphed lines 16A-16C of the line graph of FIG. 16, and specifically line 16B. This study demonstrates the capability of the disclosed blenders 110 in mitigating tribocharging for single component and multiple component pharmaceutical systems.

Figure 17B:
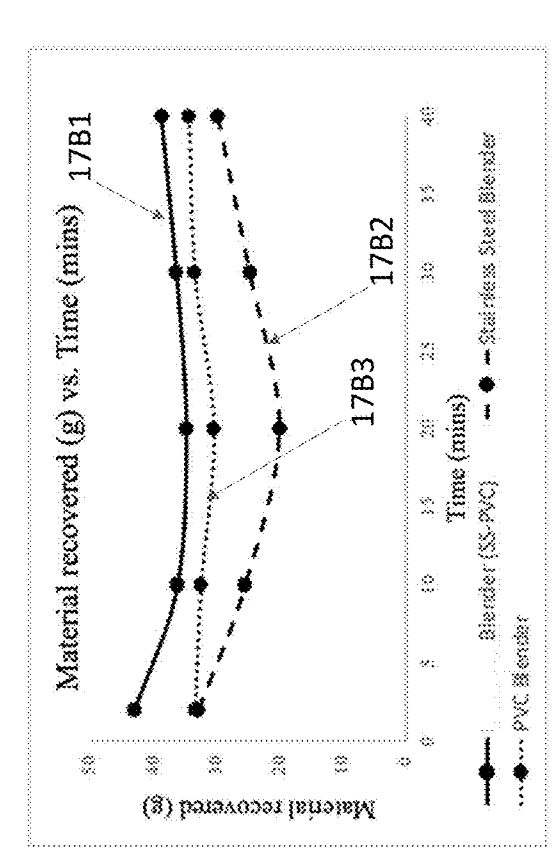
FIG. 17B shows powder addition for different blenders.
Figure 17A:
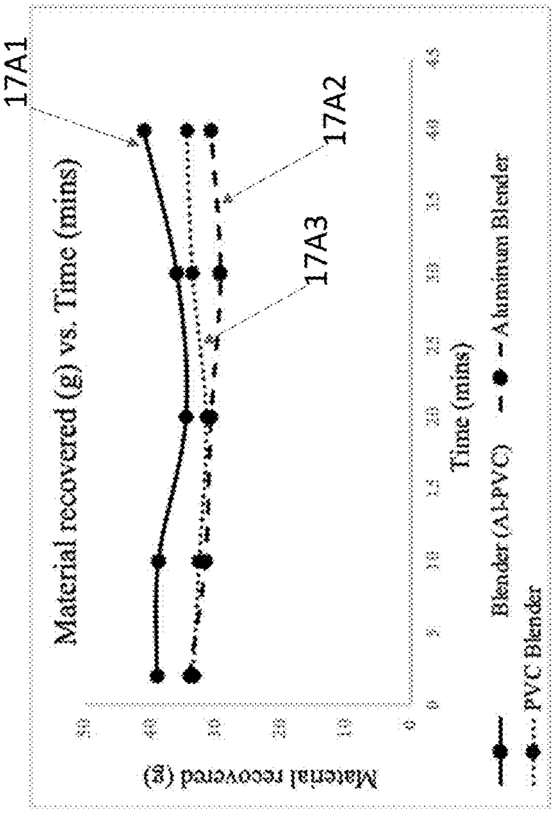
FIG. 17A shows recovered material over time for different blenders.
Figure 19C:
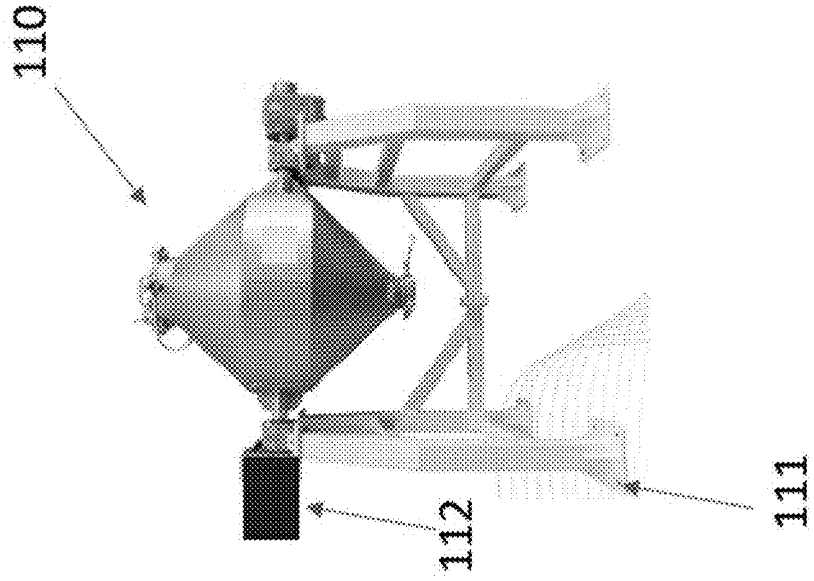
FIG. 19C shows a double cone blender having an overall shape and operational configuration that may be utilized with the disclosed embodiments.
Figure 19B:
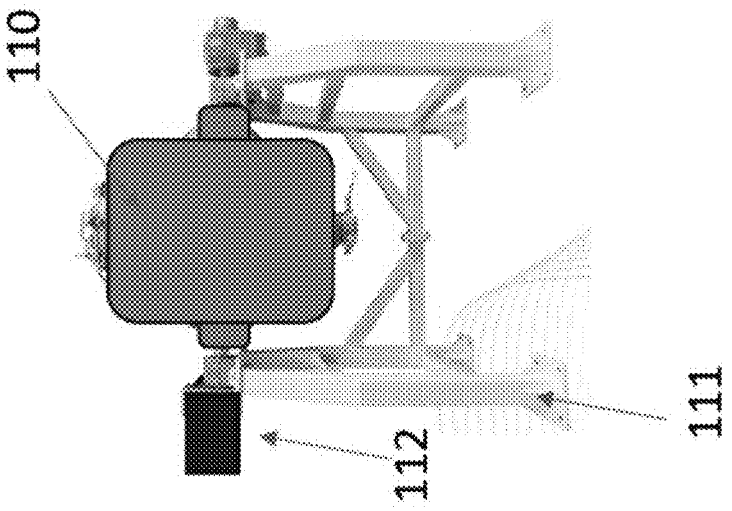
FIG. 19B shows a cylindrical blender having an overall shape and operational configuration that may be utilized with the disclosed embodiments.
Figure 19A:
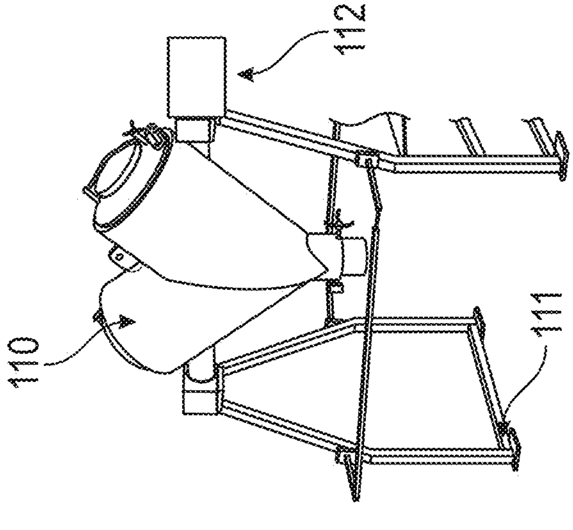
FIG. 19A shows a V-shaped blender having an overall shape and operational configuration that may be utilized with the disclosed embodiments.
Figure 19E:
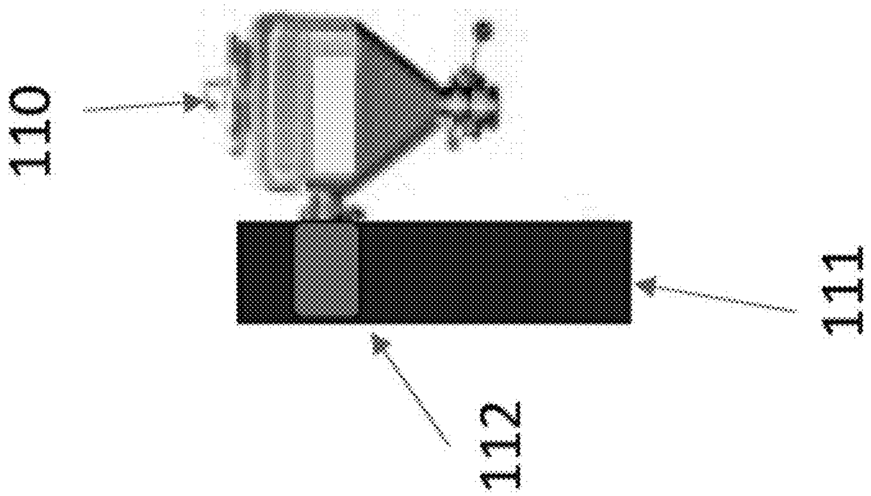
FIG. 19E shows a bin blender having an overall shape and operational configuration that may be utilized with the disclosed embodiments.
Figure 19D:
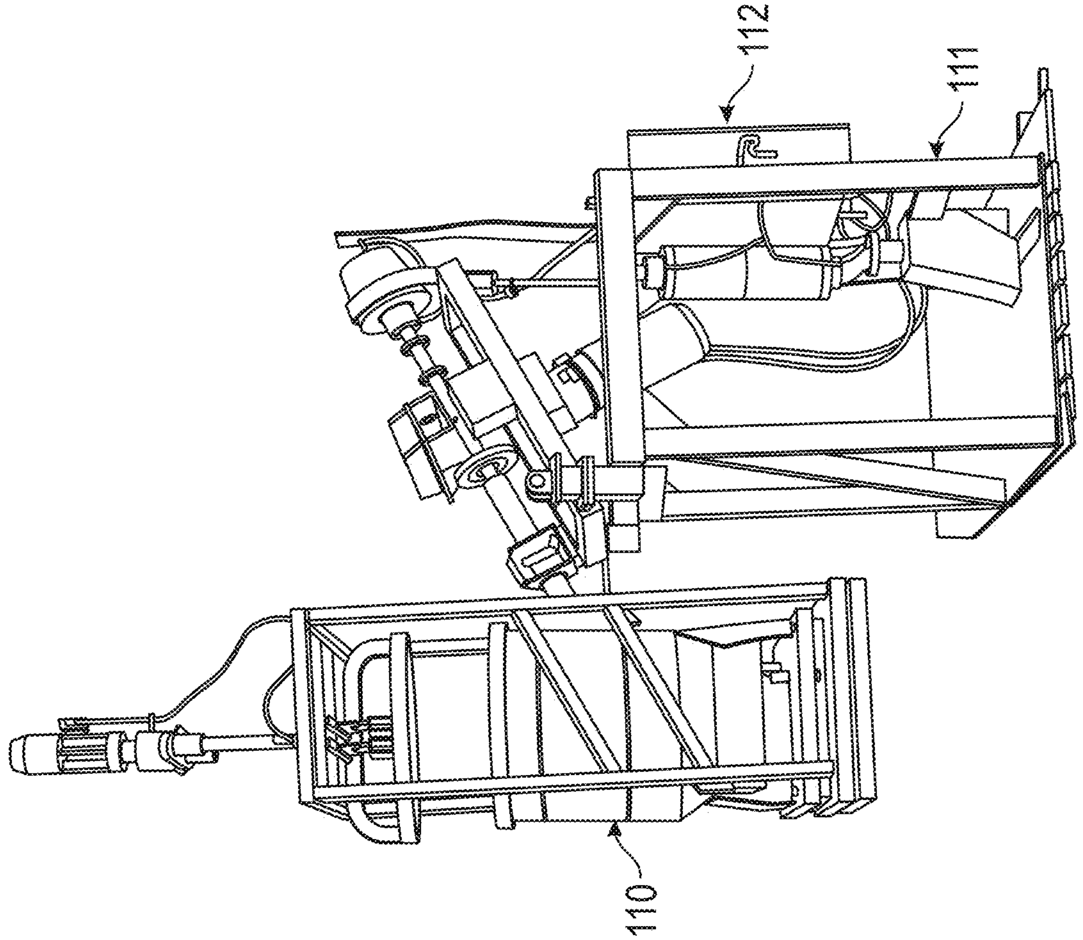
FIG. 19D shows a tote blender having an overall shape and operational configuration that may be utilized with the disclosed embodiments.

Reference will now be to FIGS. 17A, 17B and 18. To investigate the impact of using the surface of the blender on powder adhesion to the blender material, the total powder adhesion was calculated by subtracting the amount of powder recovered and initial powder weight. Due to the decreased specific charge on, e.g., ibuprofen, it was observed that there is a decrease in the powder adhesion to the blender walls using surface of the blender 110 (see FIGS. 17A and 17B). However significant adhesion was observed with metal or insulator blenders. This may be the result of significant adhesive forces between the blender wall and ibuprofen particles. The blender wall has an opposite charge as compared to ibuprofen particles therefore powder particles becomes attracted to the blender wall and deposit there due to image forces. Additionally, bipolar charging may occur due to this high level of powder adhesion which could further decrease the number of particle-blender wall collisions, further changing the powder charging dynamics.

More specifically, FIG. 17A shows a line graph of material recovered over time for the Al-PVC blender 110 with line 17A1, the aluminum blender 110 with line 17A2 and the PVC blender 110 with line 17A3. FIG. 17B shows a line graph of material recovered over time for the SS-PVC blender 110 with line 17B1, the stainless-steel blender 110 with line 17B2 and again the PVC blender 110 with line 17B3. FIG. 18A shows the unrecovered powder 140 in the aluminum (Al) blender 110. FIG. 18B1 shows the unrecovered powder 140 in the PVC arm 110A of the Al-PVC blender 110. FIG. 18B2 shows the unrecovered powder 140 in the Al arm 110A of the Al-PVC blender 110. FIG. 18C shows the unrecovered powder 140 in the PVC blender 110. FIG. 18D shows the unrecovered powder 140 in the stainless-steel (SS) blender 110. FIG. 18E1 shows the unrecovered powder 140 in the PVC arm 110A of the SS-PVC blender 110. FIG. 18E2 shows the unrecovered powder 140 in the SS arm 110A of the SS-PVC blender 110. As can be seen, the unrecovered powder 140 is less for the dual material blenders 110.

As indicated above, the disclosed V blenders could be useful to prevent powder adhesion to the blender wall. This may prevent the material loss that otherwise occurs because of powder adhesion, making the mixing process more economical.

The following terms are used to describe the invention of the present disclosure. In instances where a term is not specifically defined herein, that term is given an art-recognized meaning by those of ordinary skill applying that term in context to its use in describing the present disclosure.

The use of the terms "a" and "an" and "the" and similar referents (especially in the context of the following claims) are to be construed to cover both the singular and the plural, unless otherwise indicated herein or clearly contradicted by context. By way of example, "an element" means one element or more than one element.

It should also be understood that, in certain methods described herein that include more than one step or act, the order of the steps or acts of the method is not necessarily limited to the order in which the steps or acts of the method are recited unless the context indicates otherwise. Furthermore, the terms first, second, etc., as used herein are not meant to denote any particular ordering, but simply for convenience to denote a plurality of, for example, layers.

The terms "including", "having", "comprising", and "containing" are to be construed as open-ended terms (i.e., meaning "including, but not limited to") unless otherwise noted.

The terms "about" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "including" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "one or more," as used herein, means at least one, and thus includes individual components as well as mixtures/combinations of the listed components in any combination.

Other than in the operating examples, or where otherwise indicated, all numbers expressing quantities of ingredients and/or reaction conditions are to be understood as being modified in all instances by the term "about," meaning within 10% of the indicated number (e.g., "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material including the ingredient, wherein the raw material may be described herein to include less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A mixing vessel, comprising:

a first segment having a first work function; and a second segment having a second work function that differs from the first work function, wherein the mixing vessel is configured for mixing a powder having a third work function that is between the first and second work functions, wherein the first segment is a first arm and the second segment is a second arm that are diagonally disposed to each other, wherein the first arm has a first upper end and a first lower end and the second arm has a second upper end and a second lower end.

2. The vessel of claim 1, wherein the first segment is an insulator.

3. The vessel of claim 1, wherein the first segment comprises polymethyl methacrylate (PMMA), polyvinyl chloride (PVC), nylon, polytetrafluoroethylene-(Teflon), or a combination thereof.

4. The vessel of claim 1, wherein the second segment is a metal or an alloy.

5. The vessel of claim 1, wherein the second segment comprises aluminum, stainless steel, or a combination thereof.

6. The vessel of claim 1, wherein the mixing vessel further comprises a third segment, wherein the third segment is the insulator, metal, or alloy different than the first segment and the second segment.

7. The vessel of claim 1, wherein the first and second arms are connected in communicating relation with each other at the first and second lower ends;

the first arm and the second arm diverge upwardly from the first and second lower ends;

the first and second upper ends are open; and first and second closures are configured for removable positioned within the first and second upper ends for selectively closing the first and second upper ends of the first and second arms.

8. The vessel of claim 1, wherein the mixing vessel is a V-shaped blender, a cylindrical blender, a double cone blender, a tote blender or a bin blender.

9. The vessel of claim 1, wherein the first arm is comprised of the first segment and the second arm is comprised of the second segment.

10. The vessel of claim 1, wherein the first and second arm comprise a combination of the first segment and the second segment.

11. The vessel of claim 1, wherein the first and second arm comprise a plurality of stripes comprising the first segment and the second segment, wherein adjacent stripes comprise different segments.

12. A powder mixing device, comprising:

a stand;

a frame mounted to the stand, the frame being rotatable around a first axis of rotation;

the mixing vessel of claim 1 mounted to the frame, the mixing vessel being rotatable around the first axis of rotation; and a motor configured to rotate the frame.

13. The device of claim 12, wherein the mixing vessel is a V-shaped blender, a cylindrical blender, a double cone blender, a tote blender or a bin blender.

14. A method for mixing powders, the method comprising:

providing a powder to be mixed, wherein the powder comprises one or more active pharmaceutical ingredient, and the powder has a particle size of between 1 μm and 5000 μm;

loading the powder into the vessel of claim 1; and admixing the powder, thereby producing a powder with a charge lower than the powder mixed in a mixing device with a single component mixing vessel.

15. The method of claim 14, including maintaining a temperature range of about 68-77 F. and a relative humidity of about 30-40%.

16. A method for mixing powders, the method comprising:

providing a powder to be mixed, wherein the powder comprises one or more active pharmaceutical ingredient, and the powder has a particle size of between 1 μm and 5000 μm;

loading the powder into the device of claim 12; and
admixing the powder,
thereby producing a powder with a charge lower than the powder mixed in a mixing device with a single component mixing vessel.

17. The method of claim 16, including maintaining a temperature range of about 68-77 F. and a relative humidity of about 30-40%.

18. The method of claim 14, wherein the powder comprises acetaminophen, albuterol, piracetam, cetirizine, levetiracetam, lacosamide, levocetrizine, rotigotine, adenosine, ascorbic acid, alprostadil, amiodarone HCI, amitriptyline HCI, amlodipine besylate, ampicillin, anastrozole, apomorphine, atropine sulfate, baclofen, benzocaine, betadine, betamethasone, biotin, bromfenac, brompheniramine, budesonide, bumetanide, bupivacaine HCI, buprenorphine HCI, caffeine citrate, calcifediol, calcium gluconate, carbamazepine, cefazolin sodium, cefepime, ceftazidime, ceftriaxone sodium, cefuroxime, choline chloride, cidofovir, cephalosporin (7-aminocephalosperanic acid), ciprofloxacin, clindamycin phosphate, clonidine HCI, cyanocobalamin, cyclobenzaprine HCI, cyclosporine, cyclopentolate HCI, dehydroepianodrosterone, demercarium bromide, dexamethasone acetate, dexamethasone phosphate, dexmedetomidine, dextromethorphan hydrobromide, diazepam, diclofenac sodium, diltiazem and its salts, diphenhydramine HCI, dipyridamole, dobutamine, dopamine HCI, doxepin HCI, doxycycline, droperidol, ectoine, edetate disodium, edetate calcium disodium, ephedrine sulfate, epinephrine bitartate, estradiol, estriol, estrone, erythritol, fenbendazole, fentanyl citrate, finasteride, furosemide, gabapentin, gatifloxacin, gentamicin sulfate, glutathione, glycopyrrolate, guaifenesin, hydrocortisone and its salts, hydromorphone HCI, hydroxocobalamin HCI, hydroxyprogesterone caproate, ibuprofen, idoxuridine, inositol, isoproterenol, ketamine HCI, ketoprofen, ketorolac tromethamine, labetalol HCI, leuprolide acetate, levothyroxine sodium, lidocaine HCI, liothyronine sodium, lorazepam, medroxyprogestone acetate, meloxicam, meperidine HCI, methadone HCI, methionine, methocarbamol, methohexital sodium, methylcobalamin, methylprednisolone and its salts, metoclopramide HCI, metoprolol, midazolam HCI, milrinone, minoxidil, mitomycin, mometasone furoate, morphine sulfate, moxifloxacin HCI, N-acetylcysteine, nalbuphine HCI, naltrexone HCI, nandrolone decanoate, neostigmine methylsulfate, nicardipine HCI, nifedipine, nitroglycerin, norepinephrine bitartrate, omeprazole sodium, ondansetron, orphenadrine citrate, oseltamivir, oxymetazoline, oxytocin, pregabalin, rifampicin, shikimic acid, succinic acid, theophylline, pantoprazole, pentobarbital, phenylephrine, piroxicam, ranitidine, ropivacaine, tacrolimus, thiamine, tramadol, triamcinolone, vancomycin, verapamil, tropicamide, lactose monohydrate, D-mannitol, or cellulose.

19. The method of claim 16, wherein the powder comprises acetaminophen, albuterol, piracetam, cetirizine, levetiracetam, lacosamide, levocetrizine, rotigotine, adenosine, ascorbic acid, alprostadil, amiodarone HCI, amitriptyline HCI, amlodipine besylate, ampicillin, anastrozole, apomorphine, atropine sulfate, baclofen, benzocaine, betadine, betamethasone, biotin, bromfenac, brompheniramine, budesonide, bumetanide, bupivacaine HCI, buprenorphine HCI, caffeine citrate, calcifediol, calcium gluconate, carbamazepine, cefazolin sodium, cefepime, ceftazidime, ceftriaxone sodium, cefuroxime, choline chloride, cidofovir, cephalosporin (7-aminocephalosperanic acid), ciprofloxacin, clindamycin phosphate, clonidine HCI, cyanocobalamin, cyclobenzaprine HCI, cyclosporine, cyclopentolate HCI, dehydroepianodrosterone, demercarium bromide, dexamethasone acetate, dexamethasone phosphate, dexmedetomidine, dextromethorphan hydrobromide, diazepam, diclofenac sodium, diltiazem and its salts, diphenhydramine HCI, dipyridamole, dobutamine, dopamine HCI, doxepin HCI, doxycycline, droperidol, ectoine, edetate disodium, edetate calcium disodium, ephedrine sulfate, epinephrine bitartate, estradiol, estriol, estrone, erythritol, fenbendazole, fentanyl citrate, finasteride, furosemide, gabapentin, gatifloxacin, gentamicin sulfate, glutathione, glycopyrrolate, guaifenesin, hydrocortisone and its salts, hydromorphone HCI, hydroxocobalamin HCI, hydroxyprogesterone caproate, ibuprofen, idoxuridine, inositol, isoproterenol, ketamine HCI, ketoprofen, ketorolac tromethamine, labetalol HCI, leuprolide acetate, levothyroxine sodium, lidocaine HCI, liothyronine sodium, lorazepam, medroxyprogestone acetate, meloxicam, meperidine HCI, methadone HCI, methionine, methocarbamol, methohexital sodium, methylcobalamin, methylprednisolone and its salts, metoclopramide HCI, metoprolol, midazolam HCI, milrinone, minoxidil, mitomycin, mometasone furoate, morphine sulfate, moxifloxacin HCI, N-acetylcysteine, nalbuphine HCI, naltrexone HCI, nandrolone decanoate, neostigmine methylsulfate, nicardipine HCI, nifedipine, nitroglycerin, norepinephrine bitartrate, omeprazole sodium, ondansetron, orphenadrine citrate, oseltamivir, oxymetazoline, oxytocin, pregabalin, rifampicin, shikimic acid, succinic acid, theophylline, pantoprazole, pentobarbital, phenylephrine, piroxicam, ranitidine, ropivacaine, tacrolimus, thiamine, tramadol, triamcinolone, vancomycin, verapamil, tropicamide, lactose monohydrate, D-mannitol, or cellulose.

20. A mixing vessel, comprising: a first segment having a first work function, and a second segment having a second work function that differs from the first work function, wherein the mixing vessel is configured for mixing a powder having a third work function that is between the first and second work functions, wherein the first segment is an insulator that comprises polymethyl methacrylate (PMMA), polyvinyl chloride (PVC), nylon, polytetrafluoroethylene, or a combination thereof, the second segment is a metal or an alloy that comprises aluminum, stainless steel, or a combination thereof, the first segment is a first arm and the second segment is a second arm that are diagonally disposed to each other, the first arm has a first upper end and a first lower end and the second arm has a second upper end and a second lower end.

* * * * *